United States Patent
Hofmann et al.

(10) Patent No.: US 6,210,411 B1
(45) Date of Patent: Apr. 3, 2001

(54) HIGH FREQUENCY SURGICAL INSTRUMENT WITH A FLUID INFEED PASSAGE

(75) Inventors: Helge Hofmann, Emmingen; Gernod Fritzsch, Tuttlingen, both of (DE)

(73) Assignee: Gebrueder Berchtold GmbH & Co., Tuttlingen (DE)

( * ) Notice: Subject to any disclaimer, the term of this patent is extended or adjusted under 35 U.S.C. 154(b) by 0 days.

(21) Appl. No.: 09/305,903

(22) Filed: May 5, 1999

(30) Foreign Application Priority Data

May 11, 1998 (DE) ............................................. 198 20 995

(51) Int. Cl.[7] .................................................. A61B 18/18
(52) U.S. Cl. ................................ 606/52; 606/41; 606/49; 607/104
(58) Field of Search .......................... 606/41, 42, 45–52; 607/101–105

(56) References Cited

U.S. PATENT DOCUMENTS

| 4,096,864 |   | 6/1978 | Kletschka . |       |
|-----------|---|--------|-------------|-------|
| 4,567,890 |   | 2/1986 | Ohta .      |       |
| 5,217,460 | * | 6/1993 | Knoepfler   | 606/52 |
| 5,549,604 |   | 8/1996 | Sutcu .     |       |
| 5,603,712 | * | 2/1997 | Koranda et al. | 606/51 |
| 5,643,197 | * | 7/1997 | Brucker et al. | 604/20 |
| 5,647,871 | * | 7/1997 | Levine et al. | 606/45 |
| 6,056,747 | * | 5/2000 | Saadat      | 606/50 |

FOREIGN PATENT DOCUMENTS

| 3642077A1 | 6/1988 | (DE) . |
| 4014350A1 | 11/1991 | (DE) . |
| 4017626C2 | 7/1993 | (DE) . |
| 4416840A1 | 11/1994 | (DE) . |
| 94 18 006 U | 2/1995 | (DE) . |
| 4212053C1 | 1/1996 | (DE) . |
| 4440158A1 | 5/1996 | (DE) . |
| 0843988A1 | 5/1998 | (EP) . |
| WO9716127 | 5/1997 | (WO) . |

OTHER PUBLICATIONS

Reidenbach, H.D. *Hochfrequenz–und Lasertechnik in der Medizin*, Springer–Verlag Berlin Heidelberg New York, 1983; pp. 148–173.

* cited by examiner

*Primary Examiner*—Michael Peffley
(74) *Attorney, Agent, or Firm*—Townsend and Townsend and Crew LLP

(57) ABSTRACT

A high frequency surgical instrument which has at least one treatment electrode (11, 11', 11") which can be or is connected to a high frequency generator (12), which is at least partly fluid-permeable and to which a fluid, in particular a liquid, which counteracts the sticking of the biological tissue to the treatment electrode (11) can be or is fed in through at least one liquid infeed passage (13). At least the region (11, 11', 11") of the treatment electrode which is intended for the interaction with the biological tissue consists totally or partly of a liquid-permeable, porous, biologically compatible sinter material.

16 Claims, 5 Drawing Sheets

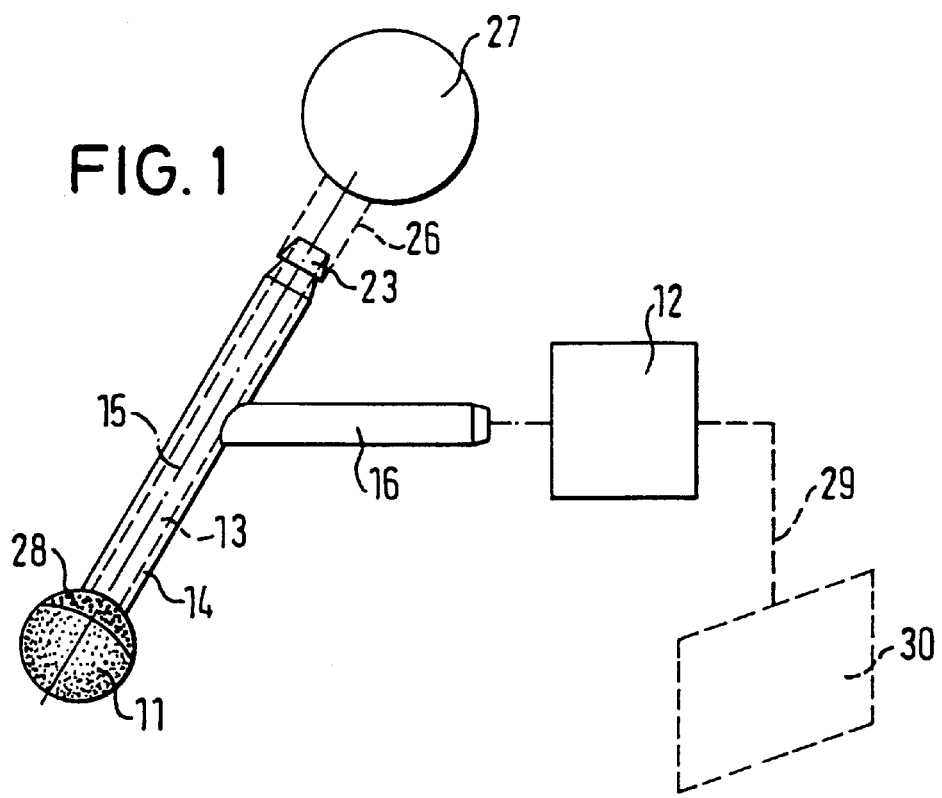
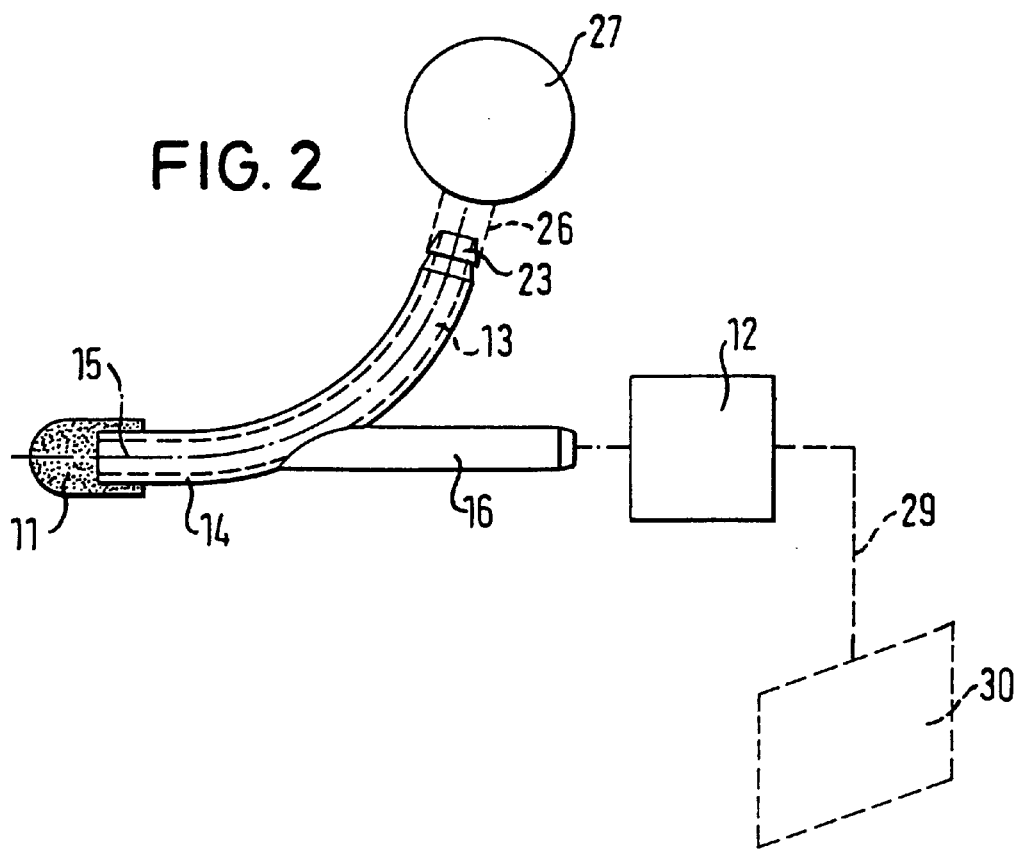

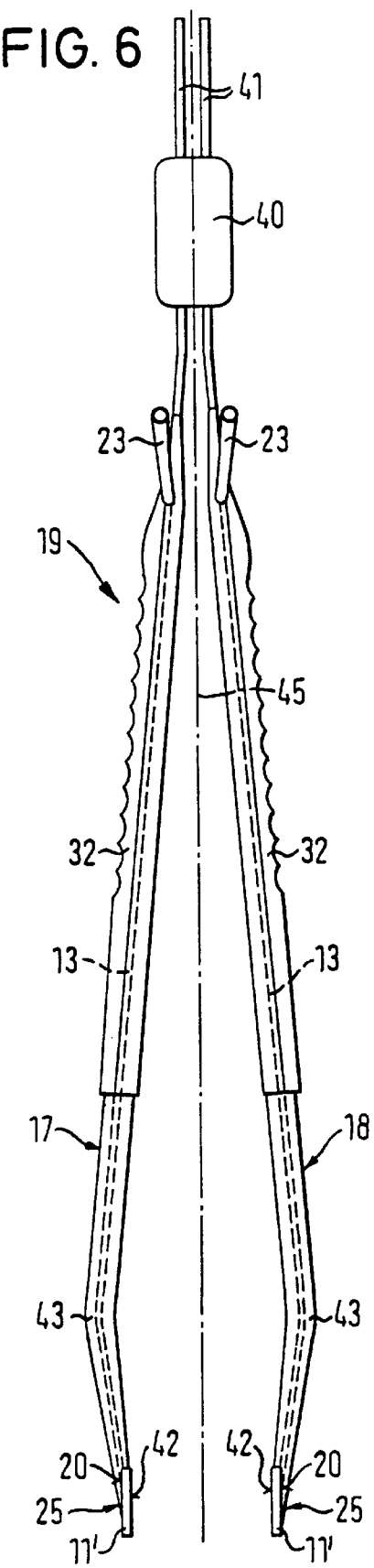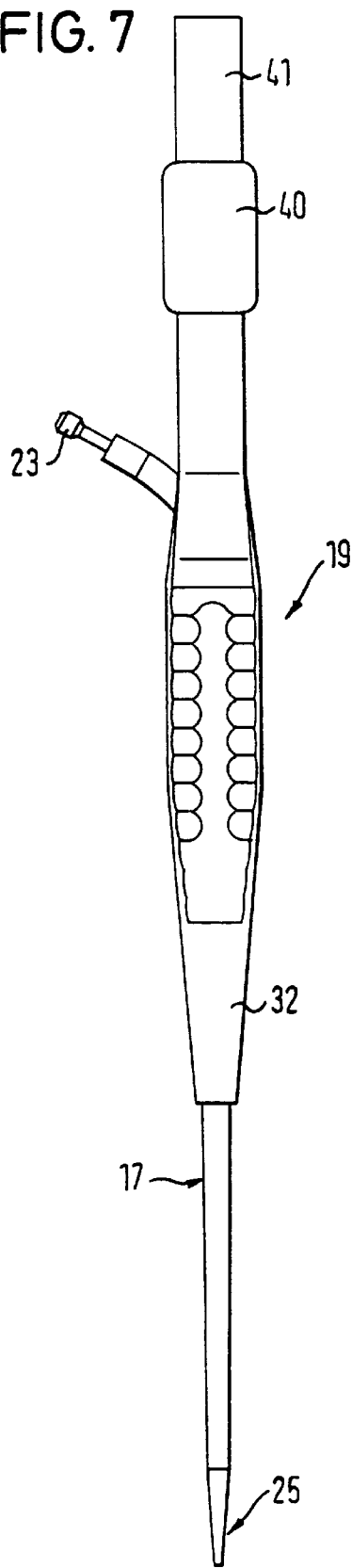

HIGH FREQUENCY SURGICAL INSTRUMENT WITH A FLUID INFEED PASSAGE

BACKGROUND OF THE INVENTION

The invention relates to a high frequency surgical instrument and in particular to high frequency surgical instruments which are intended for the coagulation of biological tissue with high frequency energy.

In the coagulation of biological tissue with high frequency energy the tissue is heated as a result of the current flow and the blood stoppage is achieved through a complex thermally activated biochemical action mechanism. This process rests mainly on the thermal conversion of the proteins in the blood from about 60° C. onwards and from the blood coagulation. Disadvantageous in this is that tissue and blood stick to the coagulation electrodes, through which the vessel in the biological tissue which had just been closed can tear open again and the current flow for the next coagulation can be hindered through the resistance increase. This sticking is influenced by a plurality of factors; the greater the electrode heating is, the stronger is the sticking.

From the book "Hochfrequenz-und Lasertechnik in der Medizin" by Reidenbach, Springer Verlag, 1983, pages 148 to 167, a method of hydrothermozation is already known in which distilled water or a saline solution emerges from bores of hollow coagulation electrodes and the sticking effect is reduced through the cooling action and/or the separation of electrode and tissue which thereby sets in. Disadvantageous in this known method is on the one hand the non-uniformity of the liquid output in the region of the treatment electrode and/or the large amount of liquid which is required for a salt jet HF coagulation and which inevitably makes the coagulation itself more difficult through its cooling action.

This principle was already used for the flushing of a bipolar coagulation forceps (DE-OS 44 40 158). Disadvantageous in this is that here as well the uniformity of the liquid output is insufficient and the flushing liquid cannot emerge between the tissue and branches of the forceps during the coagulation.

From DE-PS 42 12 053 it is known to provide a hard material layer on the electrodes, which however has only an insufficient effectiveness since the electrical impedance of the electrodes is increased and thereby higher electrical voltages are given off by the high frequency generator, which again reinforce the sticking. Anti-adhesion layers on a Teflon basis or silicon coatings (U.S. Pat No. 5,549,604) act similarly disadvantageously.

SUMMARY OF THE INVENTION

It is an object of the present invention to create a high frequency surgical instrument of the initially named kind in which the disadvantageous sticking of biological tissue during the coagulation is largely avoided without the coagulation process itself being impaired.

In accordance with the invention the liquid infeed for the actual coagulation takes place extremely finely distributedly and uniformly through a fluid-permeable, in particular liquid-permeable, porous sinter material, which preferably consists of a biologically unobjectionable, electrically conducting material, e.g. stainless steel or titanium.

The sinter material is advantageously formed as a molded body, which can e.g. be elliptical, spherical or cylindrical.

The treatment electrode, which consists at least partly of sinter material, should be formed at a hollow shaft or hose, with it being possible for the conducting in of the high frequency energy to take place either through an electrically conducting execution of the shaft or hose, through leads or through an electrically conducting fluid.

For the sake of the simple manufacture the sinter electrodes in accordance with the invention can also extend over regions which do not come into contact with the biological tissue. In this case it is expedient to partly close off the pores of the sinter material.

Expedient for the infeed of the fluid.

The application of the sinter material can take place in accordance with a particularly preferred exemplary embodiment that it is suitable for the formation of thin-walled sinter bodies at needle electrodes.

It is also possible to execute the sinter material as a ceramic body, which makes it necessary to feed in a conducting liquid to the treatment electrode, through which the high frequency energy is conducted in.

BRIEF DESCRIPTION OF THE DRAWING

FIG. 1 is a schematic view of a monopolar high frequency surgical instrument made in accordance with the invention with rectilinear fluid infeed passage, FIG. 2 is a corresponding view of a further embodiment with curved fluid infeed passage and a modified coagulation attachment, FIG. 6 is a side view of a high frequency surgical instrument in accordance with the invention which is designed as a bipolar forceps, FIG. 7 is a view which is rotated by 90° about the longitudinal axis 25 of the forceps in accordance with FIG. 6.

DESCRIPTION OF THE PREFERRED EMBODIMENT

Figure 3:
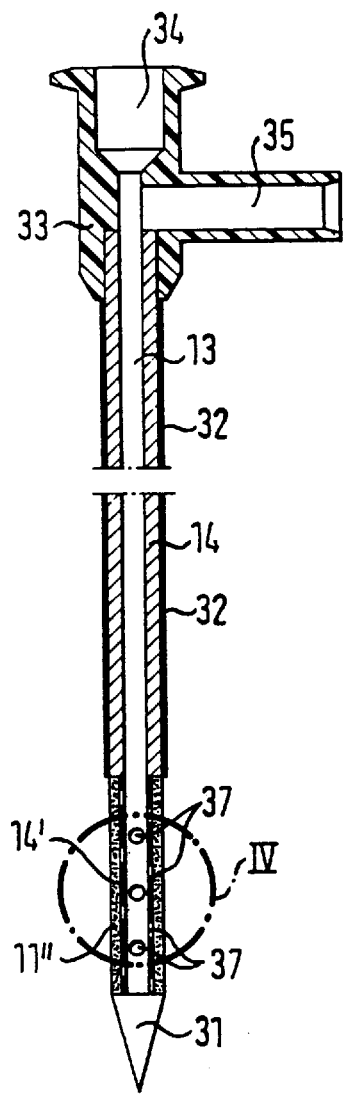
FIG. 3 is a schematic sectional view of a high frequency surgical instrument in accordance with the invention which is designed as a monopolar puncture needle electrode with cylindrical coagulation attachment.

In accordance with FIG. 1 a rectilinear fluid infeed passage 13 is provided in a hollow metal shaft 14 with a longitudinal axis 15 and is provided with a hose connection 23 at the end remote from the patient which is connected to a liquid source 27 which stands under pressure via a hose 26 which is only indicated by broken lines.

A metallic connector 16 for the electrical connection of the hollow shaft 14 to a high frequency generator 12 branches off from the hollow shaft 14 at an angle of 45°. The connection piece 16 is preferably secured in a non-illustrated electrode hand grip.

A spherical treatment electrode 11 which consists of a fluid-permeable sinter material, in particular sinter metal, is secured at the end of the hollow shaft 14 near the patient. The pores of the sinter body 11 are open forwardly and to the side, but however closed off rearwardly by a closure layer 28 in such a manner that the liquid which is fed in through the fluid infeed passage 13 can emerge only from the forward and lateral region of the treatment electrode 11.

The hollow shaft 14 protrudes into the sinter body 11 and is welded to the latter. The closure layer 28 can be formed through the application of a suitable substance or else through mechanical processing of the rear side of the sinter body 11.

In particular when the spherical treatment electrode-sinter body 11 consists of non-conducting ceramic material, a physiological, 0.9% saline solution should be used as the flushing liquid.

The treatment electrode 11 in accordance with FIG. 1 is a monopolar electrode. For this reason a neutral electrode 30 which is to be attached to the body of the patient is connected to the high frequency generator 12 via a conductor 29 which is illustrated with a broken line.

In the following figures the same reference symbols designate components corresponding to those in the exemplary embodiment in accordance with FIG. 1.

In the exemplary embodiment in accordance with FIG. 2 the hollow shaft 14 with the fluid infeed passage 13 is bent away, whereas the connection piece 16 lies in a straight line with the treatment electrode, which is formed here as a cylindrical coagulation attachment 11 with rounded-off front end.

FIG. 3 shows a monopolar puncture needle electrode, such as is e.g. used for denaturation of tumors. Behind the metallic tip 31 a thin tubular molded body 11" of sinter material is arranged on a region 14' of reduced diameter of the hollow shaft, while the part of the hollow shaft 14 lying behind it is provided with an insulation coating 32. At the end remote from the patient a plastic molded part 33 is provided in which a Luer lock connector 34 is accommodated. A high frequency connector socket 35 into which a non-illustrated high frequency connection plug can be plugged in opens laterally at the plastic molded part 33 and permits an electrical connection to be established between the non-illustrated high frequency generator and the hollow metal shaft 14. The fluid infeed passage 13 is again located centrally in the interior of the puncture needle electrode in accordance with FIG. 3.

Figure 4:
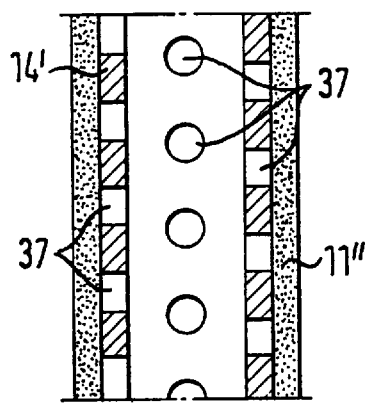
FIG. 4 is an enlarged partial view of the region IV in FIG. 3.

The region 14' of reduced outer diameter has a number of radial bores 37, as one can particularly well recognize in FIG. 4. Through the latter the liquid which is fed in at 34 can enter from the inside into the sinter-molded body 11, which is expediently applied as a coating onto the region 14' through plasma flame injections. Through the application of the porous material as a coating onto the contracted end part of the hollow metal shaft 14 which is provided with bores 37, the sinter material, which is fragile per se, is supported over a large area so well that a damage to the sinter coating during use is effectively avoided. The coating 11" preferably consists of porous stainless steel.

In the use of the treatment electrode 11 in accordance with the invention, in addition to the conducting in of voltage through the high frequency generator 12, liquid, preferably water, is also fed in through the fluid passage 13 and emerges over a large area from the pores of the sinter material 11, 11" and thus prevents a sticking of the treated biological tissue to the treatment electrode.

Figure 5:
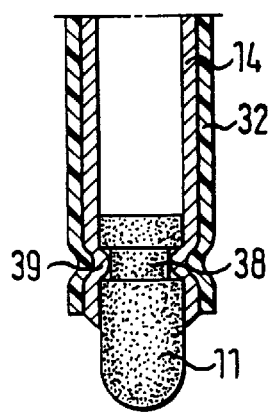
FIG. 5 shows the electrode region of a further embodiment of a high frequency surgical instrument in accordance with the invention, with form-locked securing of a sinter body representing the treatment electrode.

In accordance with FIG. 5 the treatment electrode 11, which is designed as a sinter body, consists, just as in the exemplary embodiment in accordance with FIG. 2, of a cylindrical molded body, which is rounded off at the front but which is however provided at the rear side with a circumferential groove 38, through which the rear end of the treatment electrode 11, which is introduced into the forwardly open hollow metal shaft 14, can be firmly secured to the end of the metal shaft 14 near the patient through a furrow 39 which is provided all around in the region of the circumferential groove 38.

In accordance with FIGS. 6 and 7 the two branches 17, 18 of a coagulation forceps 19 are connected mechanically to one another and electrically insulated from one another at their end which is remote from the patient through an insulating body 40. The contacts 41 which are provided for the conducting in of high frequency energy protrude out of the insulating body 40 at the rear. In or at the branches 17, 18 is located in each case a fluid infeed passage 13 which opens in the rear region into a hose connection 23 in each case.

In the rear and middle region the branches 17, 18 are provided with an insulation coating 32.

Figure 8:
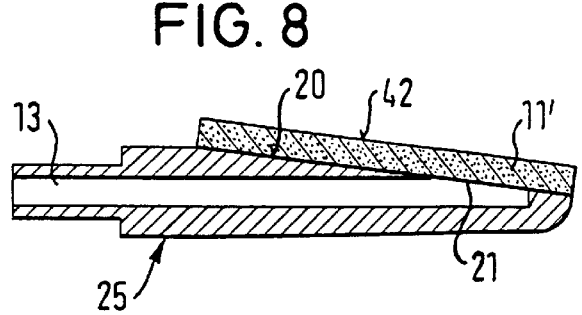
FIG. 8 is an enlarged side view of the electrode region of the branches of the forceps in accordance with FIGS. 6, 7.
Figure 9:
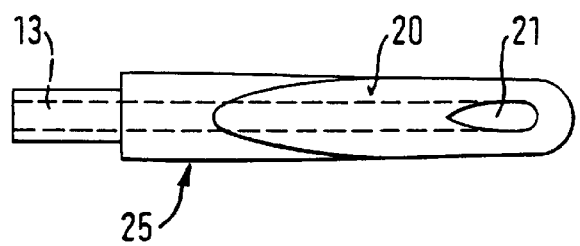
FIG. 9 is a plan view of the object in FIG. 8 with the sinter platelet removed.

As can be particularly well seen in FIGS. 8 and 9, the two branches 17, 18 are beveled in the electrode region 25 near the patient so that a planar end surface 20 which is slightly inclined outwardly arises, with the fluid infeed passage 13 opening in a fluid emergence opening 21 in the beveled end surface 20.

The beveled end surface 20 is covered in accordance with the FIGS. 6, 7 and 8 with a planar parallel platelet 11' of sinter material which is preferably welded on. In this way the liquid which is fed in through the fluid infeed passage 13 is pressed from the direction of the beveled surface 20 through the fluid emergence opening 21 into the sinter platelet 11', where it emerges uniformly distributed and uniformly from the outer actual treatment surface 42 as a result of the numerous fine pores.

In accordance with FIG. 6 the branches 17, 18 are slightly bent off inwardly near the electrode region 25 at 43 in such a manner that the planar parallel sinter platelets 11' which are placed onto the inclined end surfaces 20 have at least substantially mutually parallel treatment surfaces 42.

Figure 10:
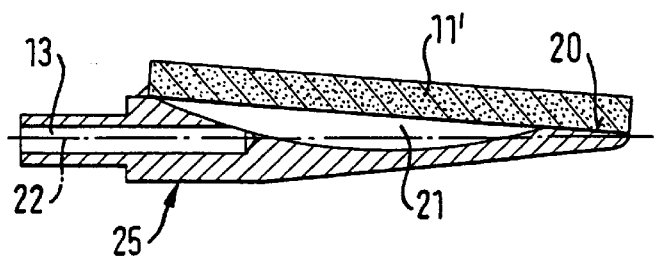
FIG. 10 is an enlarged sectional view of a further embodiment of the electrode region of the branches of the forceps in accordance with FIGS. 6, 7.
Figure 11:
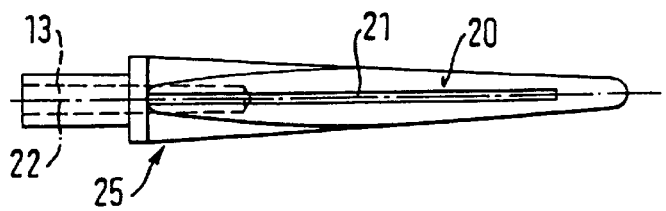
FIG. 11 is a plan view of the object in FIG. 10 with the sinter platelet removed.

FIGS. 10 and 11 show with respect to FIGS. 8 and 9 a somewhat different execution of the fluid emergence opening 21, which is formed here as a slit 21 which extends over approximately the entire length of the sinter platelet 11' so that the sinter platelet 11' is charged from the inside over a greater length with liquid than in the embodiment in accordance with FIGS. 8, 9. The slit 21 extends at least substantially parallel to the axis 22 of the electrode region 25.

Figure 13:
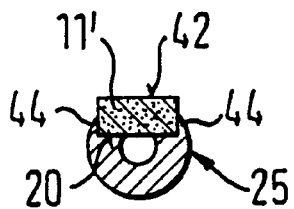
FIG. 13 is a sectional view in accordance with line XIII—XIII in FIG. 12, with the sinter platelet left out of FIG. 12 being shown in addition.
Figure 12:
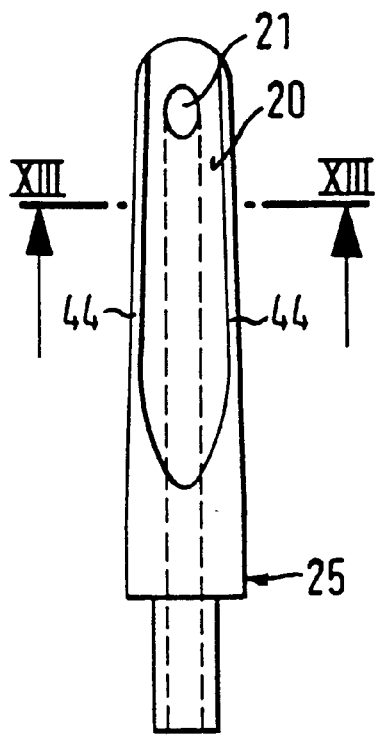
FIG. 12 is a plan view of a further embodiment of the electrode region of the branches of the forceps in accordance with FIGS. 6, 7 with the sinter platelet removed.

In the embodiment in accordance with FIGS. 12 and 13 the beveled end surface 20 of the electrode region 25 is formed as the base of a groove, the lateral webs 44 of which also support the attached sinter platelet 11' laterally so that it is particularly well protected against damage during use.

The sinter platelet 11' in accordance with FIG. 13 can be pressed into the groove, welded at the edges or otherwise secured, e.g. through adhesive bonding.

Figure 14:
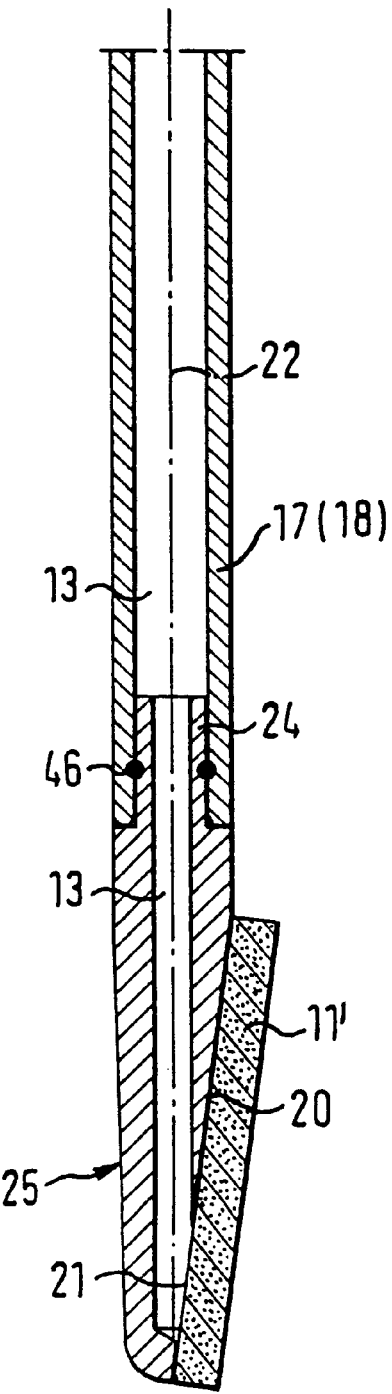
FIG. 14 is an enlarged sectional view of the electrode region of the branches of the forceps in accordance with FIGS. 6, 7, with the releasable connection of the electrode region to the branches of the forceps in accordance with FIGS. 6, 7 being reproduced in addition.

The electrode region 25 in accordance with FIG. 14, which is correspondingly also present in the embodiments in accordance with FIGS. 8 to 12, is releasably connected to the branches 17, 18 of the coagulation forceps 19. For this the electrode region 25, which contains the end of the fluid infeed passage 13, has a coaxial connector stub 24 of reduced diameter at its rearward end which has an outer diameter corresponding to the diameter of the fluid infeed passage 13 contained in the branches 17, 18. Circumferential grooves into which an O-ring 46 is laid in as sealing and snap element are located at the periphery of the connector stub 14 and in the radially oppositely lying wall of the hollow branches 17, 18. In this way the electrode region 25 can be drawn off axially from the branches 17, 18 against a latching force and latched in in the opposite direction. Thus both for cleaning and sterilization purposes as well as for repair or for the replacement of damaged sinter platelets 11' the electrode region 25 can be taken off from the branches 17, 18 of the coagulation forceps 19. The pore size of the sinter material lies between 0.5 and 150 μm.

What is claimed is:

1. High frequency surgical instrument comprising at least one hollow shaft defining at least one treatment electrode adapted to be connected to a high frequency generator, the hollow shaft having a beveled end and at least one liquid infeed passage for a liquid which counteracts a sticking of biological tissue to the treatment electrode, the beveled end forming at least one liquid emergence opening communicating with the infeed passage at least at a region of the treatment electrode which is intended for interaction with the biological tissue and comprising at least in part a liquid-permeable, porous, biologically unobjectionable sinter material which is formed as a planar platelet having a flat side secured in a liquid-impervious manner to the beveled end of the hollow shaft and which has a shape that is substantially the same as a shape of the beveled end.

2. High frequency surgical instrument in accordance with claim 1 wherein the sinter material comprises a molded body.

3. High frequency surgical instrument in accordance with claim 1 wherein the treatment electrode is electrically conducting.

4. High frequency surgical instrument in accordance with claim 3 including means releasably fastening the treatment electrode to the shaft.

5. High frequency surgical instrument in accordance with claim 3 including a hose connection at an end of the hollow shaft facing away from the treatment electrode.

6. High frequency surgical instrument in accordance with claim 1 including two treatment electrodes defining bipolar coagulation forceps and forming a bipolar arrangement.

7. High frequency surgical instrument in accordance with claim 6 wherein the planar platelet is laser welded to the beveled end of the hollow shaft.

8. High frequency surgical instrument in accordance with claim 1 wherein the fluid emergence opening comprises a slit which extends at least substantially parallel to an axis of the hollow shaft.

9. High frequency surgical instrument in accordance with claim 1 wherein the sinter material of the treatment electrode has pores, and wherein pores at specific locations where no contact with the biological tissue is to be expected or no fluid is to emerge are closed off.

10. High frequency surgical instrument in accordance with claim 9 including a layer of a material applied to the treatment electrode at the specific locations.

11. High frequency surgical instrument in accordance with claim 1 including a plurality of liquid emergence openings in the hollow shaft, and wherein the sinter material is applied as a coating over the hollow shaft and the outlet openings.

12. High frequency surgical instrument in accordance with claim 1 wherein the sinter material is a sinter metal, and including a high frequency connector connected to the sinter metal in a conducting manner.

13. High frequency surgical instrument in accordance with claim 1 wherein the sinter material is a ceramic.

14. High frequency surgical instrument in accordance with claim 1 including a saline solution in the infeed passage and the sinter material.

15. High frequency surgical instrument in accordance with claim 1 wherein the hollow shaft defines a hose.

16. High frequency surgical instrument in accordance with claim 1 wherein the hollow shaft is made of metal.

* * * * *